United States Patent [19]

Manian

[11] Patent Number: 5,565,678
[45] Date of Patent: Oct. 15, 1996

[54] RADIOGRAPHIC IMAGE QUALITY ASSESSMENT UTILIZING A STEPPED CALIBRATION TARGET

[75] Inventor: Bala S. Manian, Los Altos Hills, Calif.

[73] Assignee: Lumisys, Inc., Sunnyvale, Calif.

[21] Appl. No.: 475,138

[22] Filed: Jun. 6, 1995

[51] Int. Cl.⁶ .................................................. G01D 18/00
[52] U.S. Cl. ........................ 250/252.1; 250/582; 378/207
[58] Field of Search ...................... 250/252.1 A, 252.1 R, 250/580, 581, 582; 378/18, 207

[56] References Cited

U.S. PATENT DOCUMENTS

| | | |
|---|---|---|
| 3,604,931 | 9/1971 | Kastner et al. . |
| 4,352,020 | 9/1982 | Horiba et al. . |
| 4,400,827 | 8/1983 | Spears . |
| 4,460,832 | 7/1984 | Bigham . |
| 4,550,422 | 10/1985 | VanPelt et al. . |
| 4,759,045 | 7/1988 | Lasky . |
| 4,873,707 | 10/1989 | Robertson . |
| 5,063,583 | 11/1991 | Galkin . |
| 5,095,499 | 3/1992 | Wentz . |
| 5,172,419 | 12/1992 | Manian . |
| 5,214,578 | 5/1993 | Cornuejols et al. . |
| 5,229,585 | 7/1993 | Lemberger et al. . |
| 5,237,358 | 8/1993 | Yamada et al. . |
| 5,267,295 | 11/1993 | Strömmer . |
| 5,270,530 | 12/1993 | Godlewski et al. . |
| 5,276,726 | 1/1994 | Galkin . |
| 5,297,036 | 3/1994 | Grimaud . |
| 5,335,260 | 8/1994 | Arnold . |
| 5,406,612 | 4/1995 | Galkin ..................................... 378/207 |
| 5,420,441 | 5/1995 | Newman et al. ................. 250/252.1 X |

OTHER PUBLICATIONS

Prasad, "A Universal 'Step–Needle' Image Quality Indicator", British Journal of Non–Destructive Testing, vol. 16, No. 2, Mar. 1974, p. 49.

Chan, Heang–Ping et al., "Computer–Aided Detection of Microcalcifications in Mammograms," *Investigative Radiology*, vol. 23, No. 9, Sep., 1988, pp. 664–671.

*Primary Examiner*—Carolyn E. Fields
*Assistant Examiner*—Edward J. Glick
*Attorney, Agent, or Firm*—Thomas Schneck

[57] ABSTRACT

A system and method for performing a rapid, automatic, quantitative assessment of the image quality of a radiographic image is disclosed. The present invention utilizes a stepped calibration target made of differentially attenuating disks that is exposed to a beam of radiation simultaneously with the exposure of an object of examination. The recording medium is developed, if necessary, and the image of at least the calibration target is read, as with a laser scanner or a CCD. The optical density characteristics of the image of the calibration target are then analyzed with respect to reference optical density criteria associated with the type of recording medium used and indicative of an optimal signal pattern. If the optical density characteristics of the calibration target image meet the reference criteria, then an indication is made to show that the radiographic image has been approved as meeting the quality assurance threshold. The recording medium is typically a sheet of film, so that the approval mark may be a permanent part of the record, such as a notch in a corner of the film. The recording medium may also be a storage phosphor screen.

40 Claims, 7 Drawing Sheets

RADIOGRAPHIC IMAGE QUALITY ASSESSMENT UTILIZING A STEPPED CALIBRATION TARGET

TECHNICAL FIELD

This invention relates to quality assessment techniques for radiographic images.

BACKGROUND ART

The best clues in identifying various internal structural abnormalities are usually provided by X-ray examination. Accurate radiographic imaging is a crucial tool in detecting the often minute anomalies that can signify the early stage of a disease or weakness. Early diagnosis of a problematic condition is frequently the most powerful weapon against that condition.

Breast cancer is an example of a disease that is diagnosed relatively easily through X-ray mammography. Radiological mammograms can show minute accumulations of calcium years before such abnormalities are detectable by other noninvasive means. The mammograms themselves, however, are simply descriptive instruments, and their usefulness is limited by their precision and accuracy and by their subsequent interpretation by trained medical lpersonnel.

Because each radiographic image is a product of the conditions present at the time the image was made, variations in successive images of a single target of examination are commonplace. The intensity of the incident beam, positioning of the beam and the target, nature of the target, and the time of exposure contribute to such variations. The detailed parameters of processing the resulting film to produce a visible image add a further source of variation. Standard procedure in radiographic imaging for medical and other purposes often requires interpretation of the image, subsequent in time, by a person remote in location from the technician who has produced the radiographic image of the examination target. Therefore, the interpreter is initially required to judge the accuracy of the radiograph and then to analyze the structures presented therein. The time, expense, and possibility of error involved in this practice highlight the need for a new method wherein radiographic images can be quickly and definitively assessed for image quality and clearly marked as meeting a given quality standard.

The current state of the art includes a Quality Test Standard for X-Ray Mammograms, U.S. Pat. No. 4,759,045. This patent teaches a test tab carrying particulate material to simulate the calcium deposits present in abnormal breast tissue. The tab is affixed to the breast prior to a mammogram and an X-ray beam is simultaneously directed through both the breast tissue and the tab. Small particles are included in the tab primarily to indicate the degree of resolution of the resulting image and larger particles are included primarily to indicate its degree of contrast.

U.S. Pat. No. 5,095,499 discloses an Oriented Mammography Phantom that includes test objects, such as fibers and particles, that function as a resolution capability test, an orienting feature for placement of the phantom in the X-ray beam's imaging plane and a series of holes defining a step wedge, for use as an X-ray quality test. The step wedge portion of the phantom is further defined as a linear array of holes of differing depths and differing radiolucency. The more radiolucent the region defined by the step, the darker the image on the exposed film. The use of progressively darker filters to form a step wedge is well known in the photographic art as a means of fine-tuning image contrasts.

The phantom of the '499 patent is made of a radiolucent material of appropriate thickness to simulate the attenuation of X-ray beams that characterize the tissue being tested. Extra plates of similar radiolucent material are needed for use with the phantom if more attenuation, e.g., with a larger-sized examination target, is desired. A test film that utilizes the mammography phantom is compared, by the radiologist, to a reference film to determine the quality of the X-ray beam. Irregular image contrasts usually signal some type of equipment problems.

A test tool for X-ray system quality assurance and the manner of using the test tool are the subjects of U.S. Pat. No. 4,550,422. The test tool is a single device that contains a filter for altering an X-ray beam to produce an exposure at a certain density range, a step tablet for one step-at-a-time optical density comparisons, and written instructions on possible corrective action to be taken. The housing of the test tool contains two crossing channels, one for insertion of the test film and the other for the sliding step tablet. Matching is done by lining up the two so that their optical densities are visually similar.

In U.S. Pat. Nos. 5,063,583 and 5,276,726 to Galkin, the inventions relate to testing and standardization of film processors and correction of images for the effects of film processors. A body part is imaged and a test pattern is separately impressed on a single film. After development of the film, a visual comparison of the test pattern to a separate control pattern is needed to measure film processor performance. The image can be converted to an electrical signal and corrected for variations due to the film processor. The inventions are especially useful for accreditation of remote mammography facilities by a central governing board.

With all of the above patented devices and methods, the radiologist or other interpreter of the image is required to visually gauge the correctness of the exposure and processing steps that produced the radiograph, and to mentally adjust his analysis of the target image accordingly. Although the devices of the prior art have been found to be useful, there is a need for a more reliable alternative.

Therefore, it is an object of the present invention to provide a system and method that assesses radiographic image quality without the need for visual comparison of image patterns.

It is another object of the present invention to provide an easy to use, automated system that quickly assesses radiographic image quality.

It is yet another object to provide a permanent record, on a radiograph, indicating whether the film has undergone an assessment of image quality and whether the image quality was of a sufficiently high standard.

SUMMARY OF THE INVENTION

The above objects have been achieved through a system and method that performs a rapid, automatic quantitative assessment of the image quality of a radiographic image. The present invention employs a stepped calibration target that differentially attenuates an incident X-ray or other radiation beam and is simultaneously imaged with an examination target, i.e., a human organ or other material of which an image is desired. A recording medium containing the images of both the calibration and examination targets is developed, if necessary, and then the image of at least the calibration target is read. The recording medium is typically a sheet of film or a storage phosphor screen.

The image reader provides a quantitative signal as a function of the varying levels of optical density of the image. Analysis is then carried out by a logic segment of the image reader, specifically by comparing the obtained signal with an optimal signal pattern contained in a reference library of optimal signal patterns of the calibration target image. Since the optimum signal is dependent upon the particular specifications of the film or the storage phosphor screen, the particular signal pattern to be used for comparison purposes is selected based on the type of film or phosphor screen utilized to create the radiographic images. A user of this system or method may indicate the type of film or phosphor screen which contains the images, e.g., by entering it into the image reader, so that the calibration target is matched against the appropriate reference criteria. If the optical density levels of the calibration target image meet the reference criteria, then an indication is made to show approval of the radiographic image as having met the quality assurance threshold. This indication may be a permanent mark, such as a notch indicating approval, in the corner of the film having the images.

In accordance with the present invention, the calibration target preferably comprises a series of plates of progressively decreasing width and made of a radiation attenuating material that is stacked to form a pyramid-like structure, analogous to a step wedge used in conventional photography. The device may be a unitary or a laminated structure. If laminated, marks on each plate ensure proper alignment. In the preferred embodiment, the plates are circular and arranged in a concentric fashion with the center of the stack attenuating an incident beam more strongly than does the outer portion. Essentially, the disclosed calibration target functions as a variable density filter that creates a pattern similar to that created by a step wedge in photography. The number of plates that make up the calibration target, the material of which they are formed, and their relative dimensions are chosen to reflect the attenuation necessary for the sensitivity of the film being used and for the particular attenuation characteristics of the item under examination.

The quality of the radiographic image is dependent upon various factors, such as conditions present at the time of exposure and the steps of the development and reading processes of the recording medium. If the calibration target data is appropriately matched to the reference criteria, i.e., it provides evidence of the number, height, and width of steps or other fluctuations characteristic of the calibration target image as presented on a particular film or phosphor screen type and correctly exposed, developed, and read, then the image has met with the approval standard. Agreement of the signal with the reference criteria may be within a given range for approval.

The present invention eliminates the guesswork a radiologist or other interpreter of a radiographic image must do as to the quality of the image. The present invention is also advantageous because it requires minimal intervention of technical personnel beyond that presently required for standard production of radiographs.

BEST MODE FOR CARRYING OUT THE INVENTION

Figure 1:
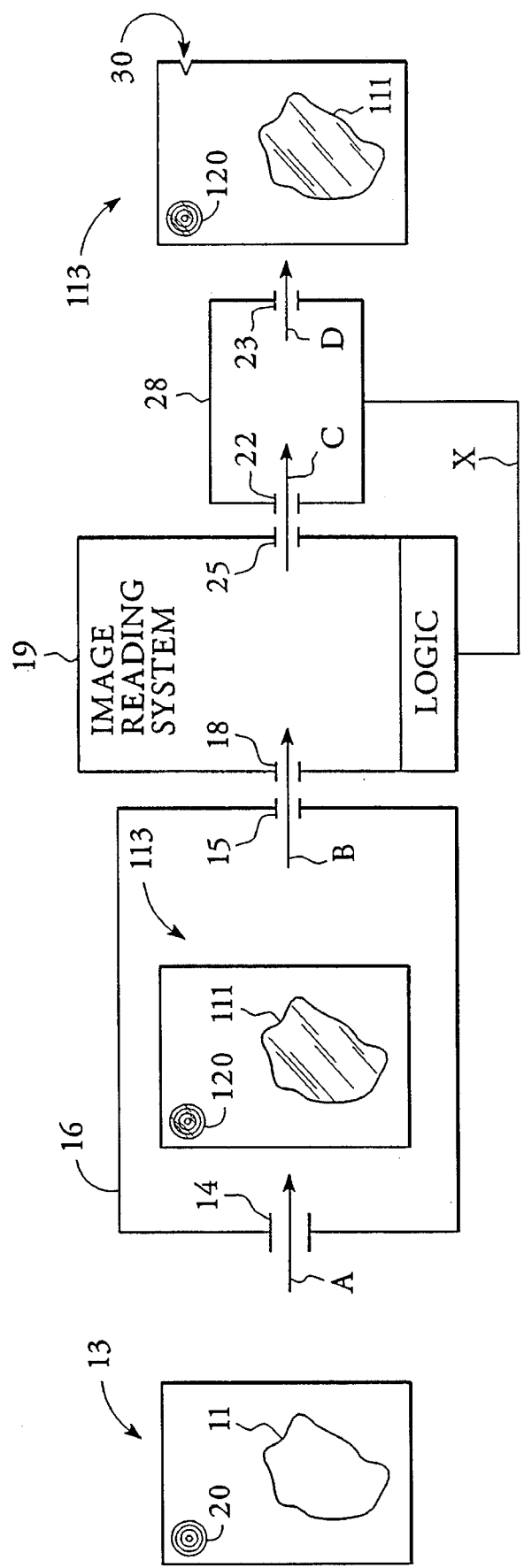
FIG. 1 is a plan view of one embodiment of the system and method of the present invention.

FIG. 1 shows a radiographic film 13, containing latent images of both calibration target 20 and examination target 11, which was obtained by simultaneously exposing both targets 20 and 11 to a beam of radiation (not shown) and collecting their image information on film. The images of the two targets should not overlap on film 13.

Film 13 is sent via entrance aperture 14 into film developer 16, as shown by arrow A. Within film developer 16, well-known chemical processing occurs to convert the latent images of calibration target 20 and examination target 11 on film 13 into the visible radiographic images 120 and 111 of the calibration and examination targets, respectively. The now developed film is designated as radiograph 113 and shown in FIG. 1 as containing shaded images. Radiograph 113 then follows arrow B and exits film developer 16 via exit aperture 15.

In FIG. 1, image reading system 19, which may be a film digitizer, is shown. Film digitizers are well-known in the prior art, e.g. see U.S. Pat. No. 5,221,848. According to one embodiment, image reader 19 includes a laser scanner that operates by sequentially scanning closely-spaced lines in an image plane in succession, as shown by scan path 40 of FIG. 7, discussed below. The light beam within image reader 19 impinges upon radiograph 113 which, after exiting film developer 16, passes into image reader 19 through aperture 18, as shown by arrow B of FIG. 1, and at least the radiographic image 120 present on radiograph 113 is read. A light source, a light collector and a detector are positioned within image reader 19 to collect and detect the variations in light transmitted through radiograph 113 and provide a quantitative signal as a function of optical density representing the image. Also within image reader 19 is a logic segment. The light detector is in communication with the logic segment, which conducts an analysis of the signal in an analog or a digital form. Variations in light transmitted to the light detector depend upon the degree of attenuation of light, from a constant intensity source, through the radiograph. A typical source is an intensity-regulated laser. The optics system within image reader 19 collects and preferably translates the information on the varying degrees of optical density present within at least the calibration target image of radiograph 113 into digital form. According to the embodiment of FIG. 1, radiograph 113 is passed through image reader 19, and the images contained therein are read and analyzed.

The information regarding the radiographic image of the calibration target is utilized by the logic segment of image reader 19 for analysis with respect to specified reference criteria on optical densities. According to the preferred embodiment of the present invention, the system is capable of operating with various film or other recording media types. Therefore, the reference criteria associated with the type of recording medium used for imaging are specified prior to analysis, as the optical density levels of a target, even under ideal exposure and development conditions, vary with recording medium type. The reference criteria may be specified, for example, by dialing in the type or by selecting the appropriate type from a menu displayed on image reader 19, the reference criteria having been entered into the logic segment of image reader 19 previously. Alternatively, the appropriate reference criteria may be selected automatically by indicating the type via a bar code present on a portion of the recording medium, in a manner analogous to the Film Cartridge Bar Code Scanner of U.S. Pat. No. 5,299,585.

According to the preferred embodiment of the present invention, radiograph 113, after being read, enters marking means 28 via entrance aperture 22, as indicated by arrow C. If the optical density data of the radiographic image of calibration target 120 meets the specified reference criteria within a reasonable degree of certainty, then the logic segment of image reader 19 sends a signal to marking means 28, as seen by line X of FIG. 1, indicating that radiograph 113 has passed the quality assurance threshold. Marking means 28 then places a distinct approval mark upon radiograph 113, such as notch 30. Radiograph 113 emerges from marking means 28 via exit aperture 23, as shown by arrow D. Alternatively, marking means 28 may be a part of image reader 19 so that the recording medium passes through the reader and is read, analyzed, and marked.

The resulting radiograph 113, if the recording has been done on film, contains a visible radiographic image 120 of calibration target 12 and a visible radiographic image 111 of the examination target 11 and, if of acceptable quality, also contains notch 30. A person examining radiograph 113 at a later time will be immediately apprised of the quality of the radiographic images present therein. The overall result of the present invention is a quantitative assessment of radiographic image quality.

The radiographic image of examination target 11 may also be read by image reader 19 and a second quantitative signal as a function of optical density representing the image of the examination target provided, along with the reading of the radiographic image of calibration target 120. Preferably, the examination target image is also digitized. The digitized image information regarding the examination target may be stored, displayed, transmitted, or duplicated.

According to the present invention, the system may also be adapted so that marking means 28 places a mark upon radiograph 113, distinct from the approval mark, to indicate that the optical density data of the radiographic image of calibration target 120 has failed to meet the appropriate reference criteria. For example, two notches may be placed on radiograph 113. This would indicate to a subsequent examiner of the radiographic image of examination target 111 that radiograph 113 has undergone processing in accordance with the present invention, but that it was not of sufficiently high quality to get an approval mark.

Figure 2:
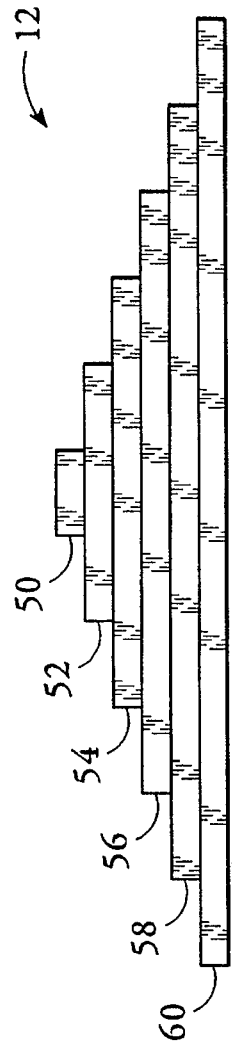
FIG. 2 is a side view of the preferred calibration target of the present invention.
Figure 3:
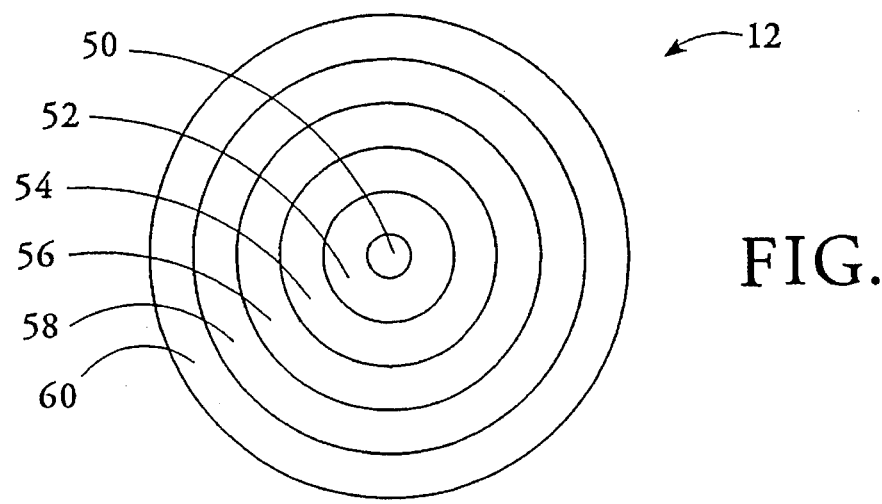
FIG. 3 is a top view of the calibration target of FIG. 2.

With reference to FIGS. 2 and 3, calibration target 12 is shown from a side view and a top view, respectively. Calibration target 12 is used to form latent image 20 and subsequently results in visible radiographic image 120. Calibration target 12 is a series of circular disks of varying radii and uniform thickness, according to the preferred embodiment of the present invention. Six disks, 50–60, are presented for illustration purposes, but a greater or fewer number may be used. The disks are preferably arranged in order of progressively decreasing radii in a concentric fashion so as to form a stepped or pyramid-like calibration target. The decrease in radii of each disk is preferably of a uniform amount. The disks are made of a material that attenuates a radiation beam.

Figure 7:
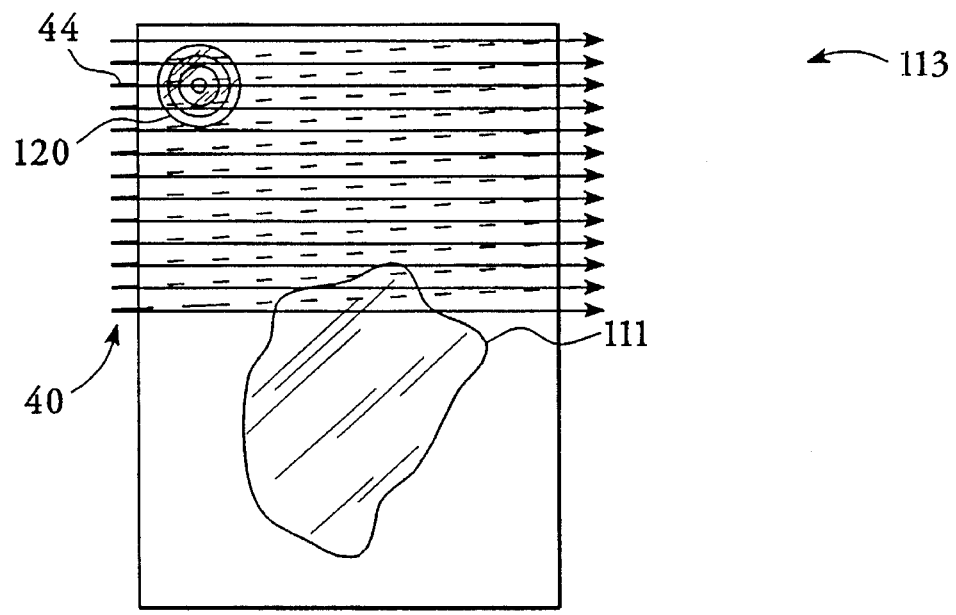
FIG. 7 is a top view of a developed film, showing a scan path in accord with the present invention.

The preferred configuration of calibration target 12 allows for a radiographic image that shows an incident beam attenuated most strongly by the center of the stack of disks and least strongly by the outer portion of the stack. The circular, symmetric shape of calibration target 12 is also preferred so as to eliminate the need to orient calibration target 12 with respect to the examination target 11 or with respect to the recording medium, when exposing the targets to the radiation beam. Regardless of the orientation of calibration target 12, one of the scan lines of scan path 40 will be directed through the center of the radiographic image 120 of the calibration target on radiograph 113 when the scan system of detection is used. In FIG. 7, scan line 44 is seen as passing through the center of radiographic image 120.

Calibration target 12 may be a laminated structure, with marks on each disk, so as to properly align each disk. Thus, the number of disks necessary for a particular purpose may be quickly changed. Calibration target 12 may also be a unitary structure. A unitary calibration target whose largest disk is approximately one inch in diameter and which is comprised of four or five disks may be practical for usage and provide significantly detailed reference criteria for the standard film types used in medical imaging, for example. Calibration target 12 may also be an integral or removable part of a recording medium holder, such as a film cassette. Positioning of the calibration target in a consistent manner in a remote, fixed location of the film cassette makes its image easily identifiable and helps to avoid overlap of the calibration and examination target images.

Figure 4:
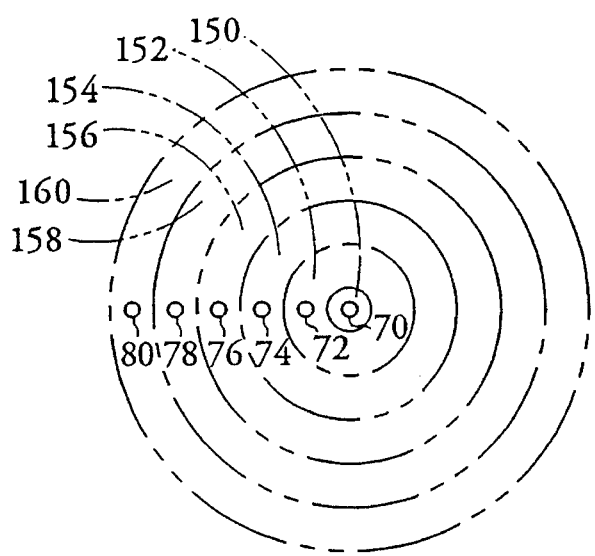
FIG. 4 is a top view of a series of point light sources, and the relative position of the image of the calibration target, according to one embodiment of the image reading system of the present invention.

With reference to FIG. 4, a series of point light sources 70–80, such as LEDs, is shown. The series of lights serves as the illumination source for another embodiment of image reader system 19. In this embodiment, each of the point light sources 70–80 is positioned to underlie a segment of the radiographic image of the calibration target corresponding to a different level of optical density. Thus, the phantom lines in FIG. 4 indicate the different segments of a typical radiographic image of a calibration target, with segment 150 corresponding to disk 50 of FIG. 3, segment 152 corresponding to disk 52 of FIG. 3, etc. The lines are shown as phantom lines in FIG. 4 because they are positioned to overlie the series of lights. The proper positioning can be effected by putting the calibration target in a fixed position, e.g. the upper left corner, relative to the recording medium and utilizing guide edges within the image reader 19 so that the reading mechanism of image reader 19 is aligned with the image of the calibration target.

In the embodiment of FIG. 4, the lights may be activated one at a time in order to easily interpret the image. For example, light 80 is activated and impinges upon the segment 160 of the image corresponding generally to the position of disk 60 in the calibration target. Since that position of the calibration target is only one disk thick, the radiation beam used for exposure will be relatively weakly attenuated and the image will be dark at that point. Typically, the variation in intensity of the illumination beam from light 80 that is produced by passage of the beam through the film containing the image is used to evaluate the image. The light passing through the image is collected and detected by one or a series of detectors which produce a signal in response to the amount of light received. This signal is a function of optical density and may be graphed, as in FIG. 5 at position 180. After a reading is made with light 80, light 80 is extinguished and light 78 is activated for the next reading, which may produce a slightly lower optical density reading as shown by 178 of FIG. 5, because light 78 corresponds to segment 158 of the image and disk 58 of the calibration target. Then light 78 is extinguished and light 76 is activated in turn, and so on through the series of lights. The low points in the graph of FIG. 5 relate to the points during which no lights in the series are activated. The resulting graph of optical densities of the calibration target's radiographic image is then compared by the logic of image reader 19 to a reference pattern. This reference pattern may be a similar graph representing the optical density levels versus time and position for a radiographic image of the calibration target exposed, developed, and read under optimum conditions. The combination of a series of point light sources, a timer for activating the lights in sequence, and a simple collection and detection system, represents an effective and inexpensive embodiment of the image reading system of the present invention.

Figure 6:
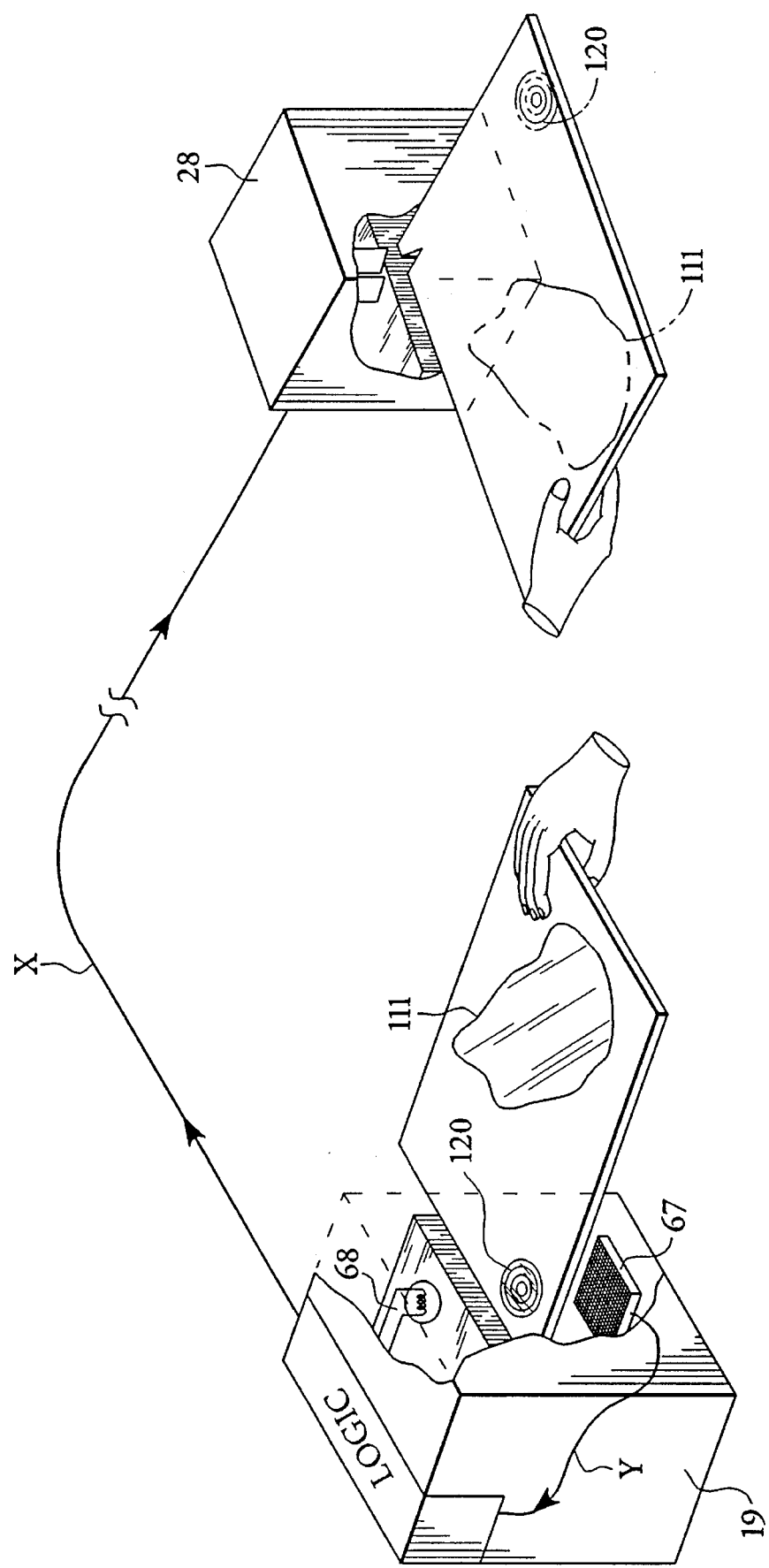
FIG. 6 depicts a second embodiment of an image reading system and one variation in the manner of presenting the radiograph to the image reading system and the marking means of the present invention.

Another embodiment is illustrated as a portion of FIG. 6. Particularly, an area-wide CCD 67 is utilized with a light source 68 within image reader 19 to assess the radiographic image 120 of the calibration target. Light passing through the image is detected by CCD 67 and a quantitative signal as a function of the optical density levels of the image are produced and sent to the logic portion of the image reader for analysis as before. A linear CCD may also be used in combination with a means for shifting the relative positions of the linear CCD and the film, for the purpose of light detection.

Additionally, FIG. 6 depicts a variation of the present invention. The image reader 19 may be a box with an entry slot (not shown) for at least a corner of the recording medium. Guides within image reader 19 allow for proper alignment of the corner of the recording medium containing the calibration target image and the image reading optics. The corner is inserted into image reader 19, the image is read, and the logic of image reader 19 conducts the analysis. The conclusion of this analysis is communicated, as shown by line X, to marking means 28. In this figure, marking means 28 is a box, similar to the box of image reader 19, with an entry slot (not shown) for at least an edge of the recording medium and two stamps for making notches in the recording medium. The user may first insert the calibration target image corner into image reader 19, and then remove it and insert an edge of the recording medium into marking means 28 for the cutting of one or two notches to indicate approval or disapproval, as shown. Alternatively, marking means 28 may be an integral part of image reader 19, so that at least a portion of the recording medium may be inserted, read, analyzed, and marked.

The manner in which the result of the quality assessment of the image is indicated may vary. For example, notches are generally most appropriate for film, because the notch may easily be cut into the film and becomes a permanent part of the film record. A simple decal may also be used. In the case of storage phosphor screens which are usually reused, the approval indication may be a light or other signal on a display panel or screen of image reader 19.

Figure 5:
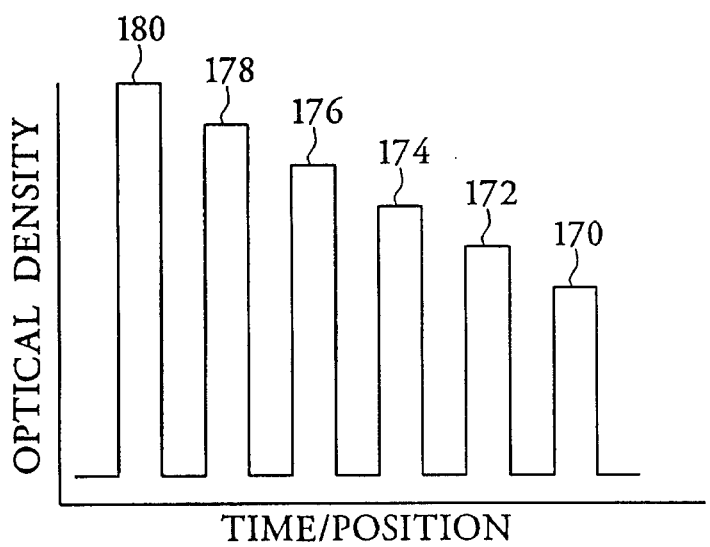
FIG. 5 is a graph of a signal related to optical density, according to the image reading system of FIG. 4.

The choice of which detection system is most appropriate within image reader 19 and which manner of presenting the recording medium to the system will depend upon considerations of cost, space, speed, sensitivity, usage volume, and additional desired functions. For example, the use of two boxes, as in FIG. 6, or a combination box, along with the point light source detection system described with regard to FIGS. 4 and 5, represents an inexpensive and compact embodiment of the system. On the other hand, a large and automated system, as in FIG. 1, wherein the film or other recording medium is passed completely through a developer, if necessary, and then through an image reader followed by a marking means, may be better suited to some applications. This embodiment may encompass reading of both the calibration and the examination targets, as with the laser scanner detection system employed in FIG. 7.

Figure 8:
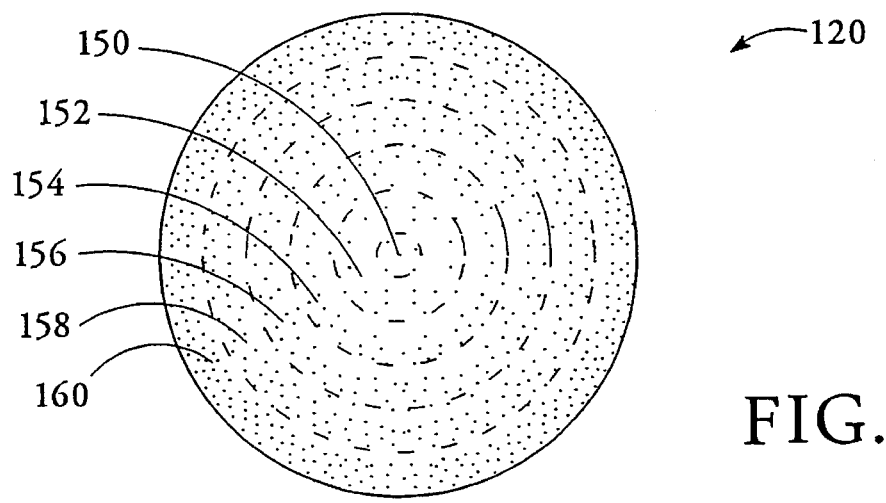
FIGS. 8–10 are top views of radiographic images of the calibration target, showing varying optical densities.
Figure 9:
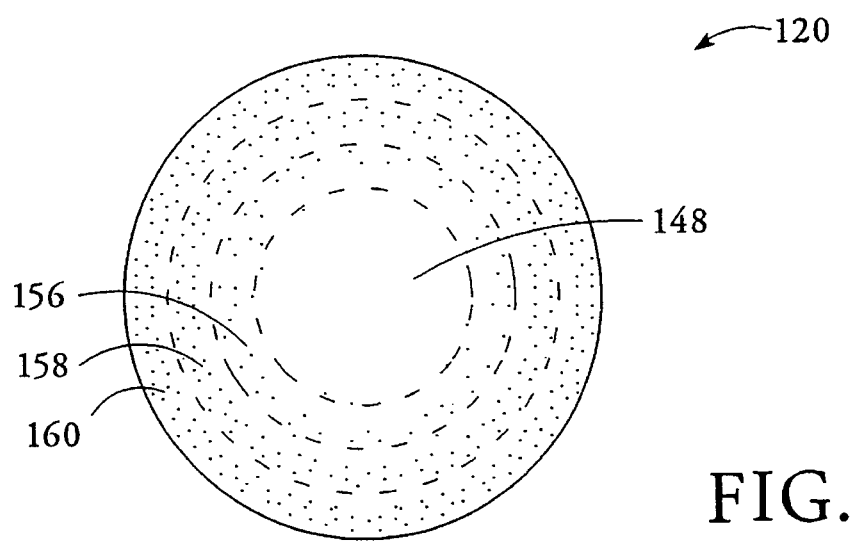
Figure 10:
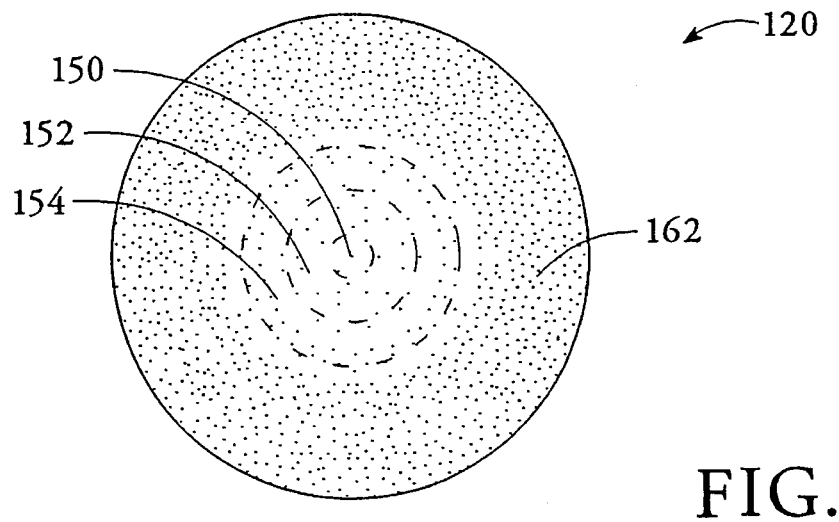

Since image quality is dependent upon variables such as the type of recording medium used and exposure and development conditions, the resulting visible radiographic image of calibration target 120 on radiograph 113 may vary, as illustrated in FIGS. 8-10. FIG. 8 shows an example of a possible pattern of optical densities according to the present invention. The pattern of disks 50–60 of calibration target 12 are distinctly visible on radiograph image 120 as rings 150–160 of generally uniform width, and each has a characteristic optical density level. FIGS. 9–10 give examples of improper imaging, wherein not all disk images and optical density levels are visible. FIG. 9 shows an image that may have resulted from inadequate exposure time of the radiation beam to calibration target 12. FIG. 10 shows an image that may have resulted from excessive exposure time of the radiation beam to the calibration target 12. Patterns such as 8–10 are presented to explain variable imaging, but in the present invention, because the radiographic images are preferably digitized, the optical density data is generally compared to the reference criteria in digital form.

Figure 11:
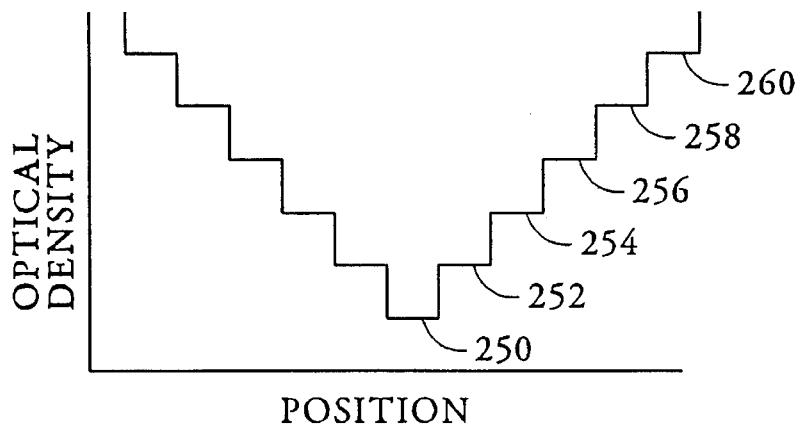
FIGS. 11–13 are graphs of signals related to the optical densities of the radiographic images of FIGS. 8–10, respectively.
Figure 12:
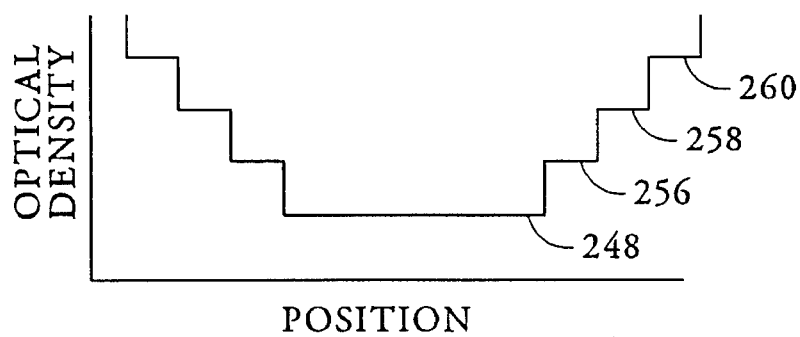
Figure 13:
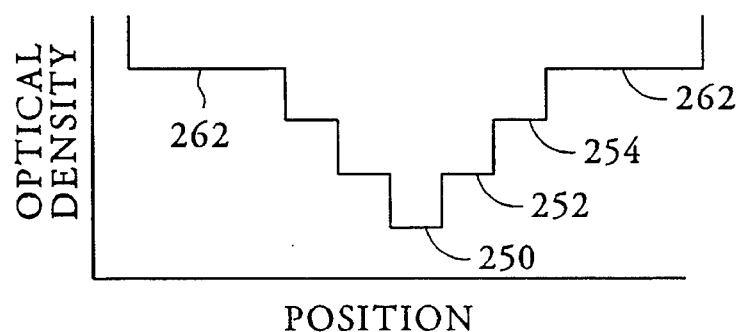

FIGS. 11–13 depict graphs of optical density versus position, corresponding to FIGS. 8–10, respectively. FIG. 11, corresponding to the radiographic image of FIG. 8, presents the digitized optical density data of FIG. 8 in graphic form. Each step 250–260 of FIG. 11 is of generally uniform width and matches each ring 150–160 of FIG. 8. FIG. 11 may represent digitized optical density data that matches a given set of reference criteria. The optical densities of step 250 and ring 150 are lowest because they correspond to the center disk 50 of calibration target 12, as seen in FIG. 3, which is the most strongly attenuating portion of calibration target 12. Similarly, step 260 and ring 160 show high levels of optical density and correspond to the outermost portion 60 of calibration target 12, as seen in FIG. 3. FIGS. 12 and 13 do not show all possible steps corresponding to all disks 50–60 present in calibration target 12, and the steps they do show are not uniform in width. FIGS. 12 and 13 may represent digitized optical density data that fails to meet the selected reference criteria.

Figure 14:
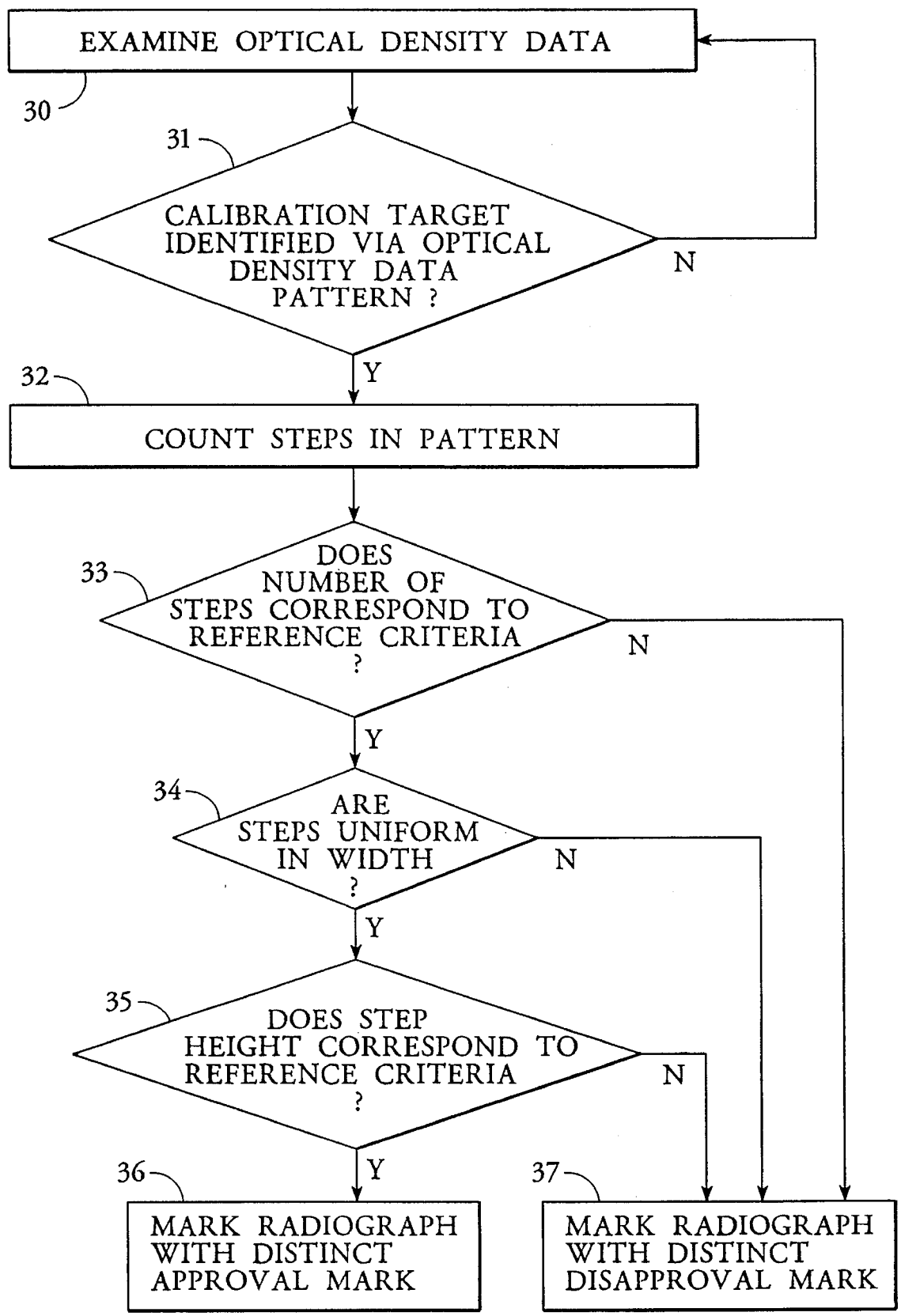
FIG. 14 is a flow chart representing an analysis procedure in accordance with the present invention.

An algorithm for analysis of digitized optical density data, as shown in the example of FIG. 14, may be set up within the logic segment of image reading system 19. The digitized optical density data is examined 30 to identify 31 the radiographic image 120 of the calibration target. The identification is possible because the optical density data corresponding to radiographic image 120 will have a characteristic pattern indicative of the pyramid-like structure of calibration target 12. After identification, that portion of the optical density data corresponding to radiographic image 120 of the calibration target is analyzed more closely. The number of data variations that simulate "steps" of calibration target 12 are counted 32 and compared 33 to the steps present in the specified reference criteria. If a match of the number of steps does not occur, a signal is sent to marking means 28 to mark 37 radiograph 113 with a distinct disapproval mark. If the number of steps matches, then further inquiry is made 34 as to whether the steps are uniform in width. If they are not uniform, radiograph 113 is marked 37 with a distinct disapproval mark. If the steps are uniform, the next step in the analysis is to compare 35 the step heights to the specified reference criteria. A failure to match sends a signal to marking means 28 to mark 37 radiographic 113 with a distinct disapproval mark. A match of the reference criteria and radiographic image 120 of the calibration target with respect to the step size and the number of steps sends a signal to marking means 28 to mark 36 radiograph 113 with a distinct approval mark. The analysis may be conducted so that the signal meets the referenced optimal signal pattern if it is within a given approval range.

Figure 15:
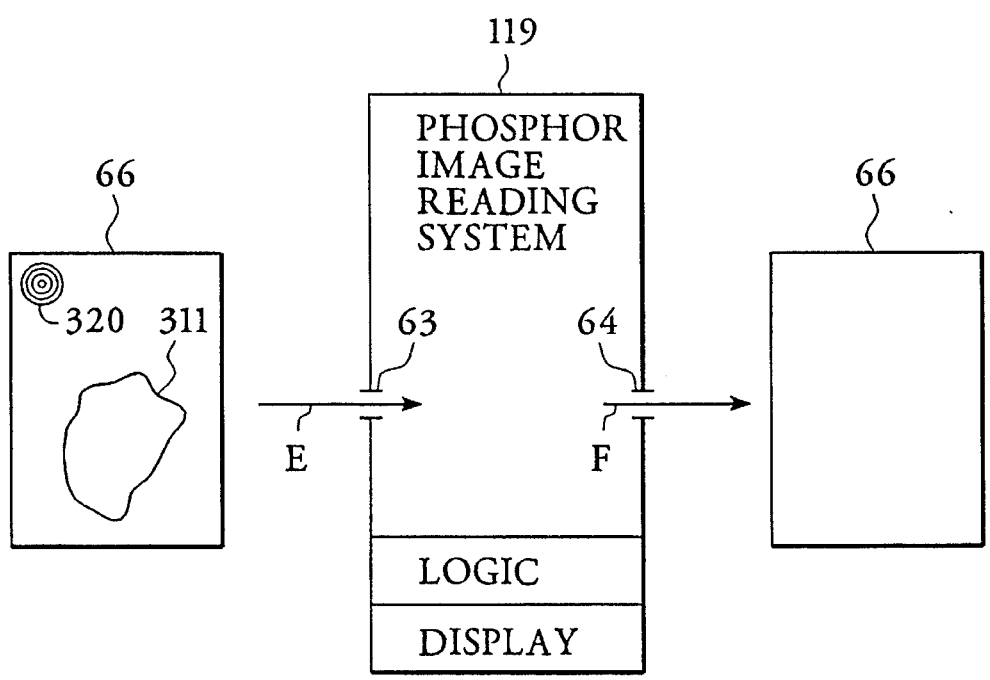
FIG. 15 is a plan view of a second embodiment of the system and method of the present invention.

If the recording medium utilized is a storage phosphor screen, then separate development and reading steps are unnecessary. The calibration target and the examination target are spaced apart and simultaneously exposed to a beam of radiation to form latent images on a phosphor screen. FIG. 15 shows a phosphor screen 66 having a calibration target latent image 320 and an examination target latent image 311. As is well-known, the latent images stored on the phosphor screen are read by illumination of the phosphor screen, followed by collection and detection of the resulting phosphorescent emission.

The phosphor screen 66 of FIG. 15 is inserted, as seen by arrow E, through aperture 63 of the phosphor image reading system 119. Inside phosphor image reading system 119, the images of at least the calibration target and preferably both the calibration and examination targets are read, as by the laser scanner system described above. In a phosphor screen reader, however, the light collection optics are likely to be different than in a film image reader. The logic section of phosphor screen reader 119 performs the analysis of the calibration target image, as before, by comparing the image with reference criteria stored within the system. A display screen may be utilized as a part of phosphor screen reader 119, for display of both the images read from the screen and the results of the quality assurance assessment. The phosphor screen exits phosphor screen reader 119 through aperture 64, as indicated by arrow F, once the latent images have been read. Typically, phosphor screen 66 is then ready for reuse.

Figure 16:
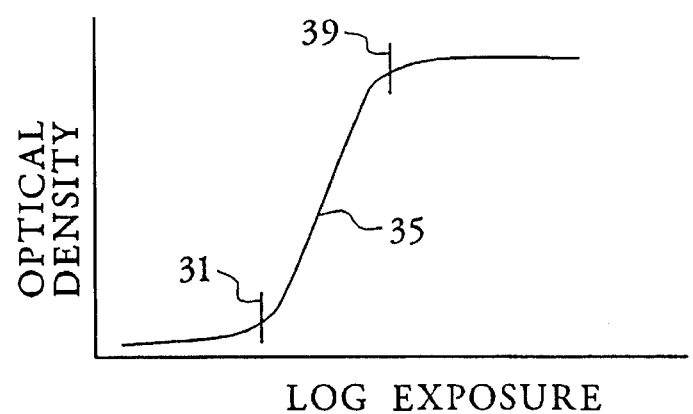
FIG. 16 is a graph of the optical density versus log of exposure of a calibration target of the present invention.

FIG. 16 illustrates the relation between optical density and the log of exposure. Proper imaging requires exposure in linear region 35 between marks 31 and 39.

As stated above, another embodiment of the present invention allows for direct analysis of radiograph 113 without digitization. In this embodiment, image reader 19 reads the images and its logic segment analyzes the quantitative signal corresponding to the radiographic image 120 of the calibration target in analog form, with respect to reference criteria associated with the type of recording medium used. The logic segment may perform an algorithm similar to that presented in FIG. 14. The radiographic image 120 of the calibration target is identified via a characteristic signal pattern and compared with specified reference criteria. The reference criteria are presented as a signal pattern of the calibration target 12 on a particular type of film and under ideal exposure and development conditions.

I claim:

1. A system for quantitatively assessing image quality on a radiographic image recording medium having images of an examination target and of a calibration target of differentially attenuating regions, the system comprising:

means for reading the image of the calibration target from the recording medium with light and providing a quantitative signal as a function of optical density representing the image of the calibration target, means for receiving and analyzing the signal with respect to reference criteria associated with the recording medium and indicative of an optimal signal pattern, and means for indicating whether the signal meets the reference criteria.

2. The system of claim 1 wherein the means for indicating comprises means for marking the recording medium with a first distinct mark if the signal meets the reference criteria.

3. The system of claim 1 wherein the means for indicating comprises means for marking the recording medium with a second distinct mark if the signal fails to meet the reference criteria.

4. The system of claim 1 wherein the means for reading with light and providing a signal comprises a laser scanner, and a light collector and detector.

5. The system of claim 1 wherein the means for reading with light and providing a signal comprises a light source, and an area-wide CCD.

6. The system of claim 1 wherein the means for reading with light and providing a signal comprises a light source, a linear CCD, and means for shifting relative positions of the recording medium and the CCD.

7. The system of claim 1 wherein the means for reading with light and providing a signal comprises a series of point light sources, at least one point light source positioned to illuminate a segment of the image of the calibration target corresponding to one of the series of differentially attenuating regions, and a light collector and detector.

8. The system of claim 7 further comprising:

means for activating the series of point light sources in sequence.

9. The system of claim 7 wherein the detector comprises a series of detection cells, each detection cell positioned to receive light from one of the point light sources.

10. The system of claim 1 further comprising:

means for reading the image of the examination target from the recording medium with light and providing a second quantitative signal as a function of optical density representing the image of the examination target.

11. The system of claim 1 wherein the quantitative signal is in digital form.

12. A radiographic image quality assessment system comprising:

a film cassette having a calibration target with a series of differentially attenuating regions, the cassette being adapted for holding a sheet of film during exposure of an examination target, the calibration target, and the sheet of film to radiation, means for developing the exposed sheet of film so as to form a radiograph having visible radiographic images of the examination target and of the calibration target, means for reading the visible radiographic image of the calibration target with light and providing a quantitative signal as a function of optical density representing the image of the calibration target, means for receiving and analyzing the signal with respect to reference criteria associated with the film and indicative of an optimal signal pattern, and means for indicating whether the signal meets the reference criteria.

13. The system of claim 12 wherein the means for indicating comprises means for marking the radiograph with a first distinct mark if the signal meets the reference criteria.

14. The system of claim 12 wherein the means for indicating comprises means for marking the radiograph with a second distinct mark if the signal fails to meet the reference criteria.

15. The system of claim 12 wherein the calibration target is an integral part of the film cassette.

16. The system of claim 12 wherein the calibration target is removably attached to the film cassette.

17. The system of claim 12 wherein the calibration target is positioned in a remote fixed location of the film cassette so that the visible radiographic images of the examination target and the calibration target do not overlap on the radiograph and the image of the calibration target is easily identifiable.

18. The system of claim 12 wherein the series of differentially attenuating regions of the calibration target comprise a series of plates of progressively decreasing width.

19. The system of claim 18 wherein the series of plates comprises a series of circular disks of progressively decreasing radii.

20. The system of claim 19 wherein the disks are arranged in a concentric fashion.

21. The system of claim 18 wherein the plates have uniform thickness.

22. The system of claim 18 wherein the plates have alignment marks.

23. The system of claim 12 wherein the means for reading with light and providing a signal comprises a laser scanner, and a light collector and detector.

24. The system of claim 12 wherein the means for reading with light and providing a signal comprises a light source, and an area-wide CCD.

25. The system of claim 12 wherein the means for reading with light and providing a signal comprises a light source, a linear CCD, and means for shifting relative positions of the radiograph and the CCD.

26. The system of claim 12 wherein the means for reading with light and providing a signal comprises a series of point light sources, at least one point light source positioned to illuminate a segment of the image of the calibration target corresponding to one of the series of differentially attenuating regions, and a light collector and detector.

27. The system of claim 26 further comprising:

means for activating the series of point light sources in sequence.

28. The system of claim 26 wherein the detector comprises a series of detection cells, each detection cell positioned to receive light from one of the point light sources.

29. The system of claim 12 further comprising:

means for reading the visible radiographic image of the examination target with light and providing a second quantitative signal as a function of optical density representing the image of the examination target.

30. The system of claim 12 wherein the quantitative signal is in digital form.

31. A method for quantitatively assessing the image quality of a radiographic image of an examination target, the method comprising:

directing a beam of radiation simultaneously through a calibration target having a series of differentially attenuating regions and an examination target and onto a film, developing the film so as to convert the film into a radiograph having visible radiographic images of the calibration target and of the examination target, reading the radiographic image of at least the calibration target with light and providing a quantitative signal as a function of optical density representing the image, receiving and analyzing the signal corresponding to the radiographic image of the calibration target with respect to reference criteria associated with the film and indicative of an optimal signal pattern, and indicating whether the signal meets the reference criteria.

32. The method of claim 31 wherein the step of receiving and analyzing the signal further comprises selecting the reference criteria based on the type of film used to create the radiograph from a reference library of prerecorded optimal signal patterns for the calibration target, and comparing the signal corresponding to the radiographic image of the calibration target with the selected reference criteria for agreement of the signal with the selected optimal signal pattern.

33. The method of claim 32 wherein the step of comparing the signal with the selected reference criteria further comprises comparing for agreement in number, width, and height of fluctuations between the signal and the selected optimal signal pattern.

34. The method of claim 31 further comprising:

marking the radiograph with a first distinct mark if the signal corresponding to the radiographic image of the calibration target meets the reference criteria.

35. The method of claim 31 further comprising:

marking the radiograph with a second distinct mark if the signal corresponding to the radiographic image of the calibration target fails to meet the reference criteria.

36. The method of claim 31 wherein the step of reading with light and providing a quantitative signal translates the image to digital form.

37. A method for quantitatively assessing the image quality of a radiographic image of an examination target, the method comprising:

directing a beam of radiation simultaneously through a calibration target having a series of differentially attenuating regions and an examination target and onto a storage phosphor screen to form latent images of the calibration and examination targets, reading the latent image of at least the calibration target with light and providing a quantitative signal as a function of optical density representing the image, receiving and analyzing the signal corresponding to the image of the calibration target with respect to reference criteria associated with the phosphor screen and indicative of an optimal signal pattern, and indicating whether the signal meets the reference criteria.

38. The method of claim 37 wherein the step of receiving and analyzing the signal further comprises selecting the reference criteria based on the type of phosphor screen used, from a reference library of prerecorded optimal signal patterns for the calibration target, and comparing the signal corresponding to the image of the calibration target with the selected reference criteria for agreement of the signal with the selected optimal signal pattern.

39. The method of claim 38 wherein the step of comparing the signal with the selected reference criteria further comprises comparing for agreement in number, width, and height of fluctuations between the signal and the selected optimal signal pattern.

40. The method of claim 37 wherein the step of reading with light and providing a quantitative signal translates the image to digital form.

* * * * *